(12) United States Patent
Gonzalez-Hernandez

(10) Patent No.: US 8,075,575 B2
(45) Date of Patent: Dec. 13, 2011

(54) DEVICE AND METHOD FOR ASSISTING IN FLEXOR TENDON REPAIR AND REHABILITATION

(75) Inventor: Eduardo Gonzalez-Hernandez, Coconut Grove, FL (US)

(73) Assignee: Toby Orthopaedics, LLC, Miami, FL (US)

( * ) Notice: Subject to any disclaimer, the term of this patent is extended or adjusted under 35 U.S.C. 154(b) by 673 days.

(21) Appl. No.: 11/962,867

(22) Filed: Dec. 21, 2007

(65) Prior Publication Data

US 2009/0048616 A1 Feb. 19, 2009

Related U.S. Application Data

(60) Provisional application No. 60/955,729, filed on Aug. 14, 2007.

(51) Int. Cl.
A61B 17/04 (2006.01)
(52) U.S. Cl. ...................................... 606/148
(58) Field of Classification Search .......... 606/139–143, 606/151–156, 108; 128/898; 623/13.11–13.2, 623/1.23; 600/201, 210, 235
See application file for complete search history.

(56) References Cited

U.S. PATENT DOCUMENTS

| | | | |
|---|---|---|---|
| 3,842,441 A | 10/1974 | Kaiser | |
| 4,584,722 A | 4/1986 | Levy et al. | |
| 4,733,850 A | 3/1988 | Thompson | |
| 4,781,191 A * | 11/1988 | Thompson | 606/151 |
| 5,651,790 A | 7/1997 | Resnick et al. | |
| 5,803,904 A * | 9/1998 | Mehdizadeh | 600/235 |
| 5,893,861 A | 4/1999 | Yumoto | |
| 5,897,591 A | 4/1999 | Kobayashi | |
| 6,033,361 A | 3/2000 | Co et al. | |
| 6,033,561 A | 3/2000 | Co et al. | |

(Continued)

FOREIGN PATENT DOCUMENTS

EP 1 757 231 A1 2/2007

(Continued)

OTHER PUBLICATIONS

U.S. Appl. No. 12/807,962, filed Sep. 2010, Gonzalez-Hernandez.
U.S. Appl. No. 61/403,116, filed Sep. 2010, Gonzalez-Hernandez Biologically Oriented Prostheses (BIOPRO); Tendonel® product brochure; 2 pages. .

(Continued)

Primary Examiner — Melanie Tyson
(74) Attorney, Agent, or Firm — Martin & Ferraro, LLP

(57) ABSTRACT

A surgical device and method used to assist in the surgical repair and rehabilitation of damaged and/or severed tendons. In one embodiment of the present invention, the device includes a hollow member, preferably shaped as a partial funnel and/or cone, having an inner and outer surface, a flared mouth, a shaft, and an apical end. In another embodiment, the device includes a hollow member, preferably shaped as funnel or barrel cut in half along its longitudinal axis, having an inner and outer surface, two flared mouths, and a shaft. The device may further include a thin, elongated handle for ease of manipulation, and can be implantable or non-implantable. The present invention further discloses a method of passing a severed flexor tendon and/or repair site through the edge of a pulley in the flexor tendon sheath, wherein the hollow member of the device disclosed in the present invention is introduced into the edge of a flexor tendon sheath's pulley and a severed tendon end and/or repair site is passed through the flared mouth of the device and is gently compressed through the shaft and apical end of the device so that the tendon end or repair site can be simultaneously squeezed into the pulley in a smooth and non-damaging manner.

23 Claims, 19 Drawing Sheets

U.S. PATENT DOCUMENTS

| | | | |
|---|---|---|---|
| 6,984,241 | B2 | 1/2006 | Lubbers et al. |
| 7,112,221 | B2 | 9/2006 | Harris |
| 7,144,424 | B2 | 12/2006 | Steenlage |
| 2005/0033338 | A1 | 2/2005 | Ferree |
| 2005/0228426 | A1* | 10/2005 | Campbell ................... 606/192 |
| 2008/0109021 | A1 | 5/2008 | Medoff |
| 2010/0137883 | A1 | 6/2010 | Gonzalez-Hernandez |

FOREIGN PATENT DOCUMENTS

| | | |
|---|---|---|
| GB | 2 424 372 A | 9/2006 |

OTHER PUBLICATIONS

Kamath, B. Jagannath, et al.; Technique Article; A Simple, Semirigid, and Surgeon-Friendly Tendon Retriever and Flexor Shealth Dilator; The Journal of Hand Surgery, vol. 32A, No, 2, Feb. 2007, pp. 269-273.

Sourmelis, S.G., et al.; Retrieval of the Retracted Flexor Tendon; Journal of Hand Surgery (British and European Volume), vol. 12-B, No. 1, Feb. 1987, cover page and pp. 109-111.

Supplementary Partial European SEarch Report, Application No. EP 08 82 7278; mailed Jun. 30, 2011; 6 pages.

* cited by examiner

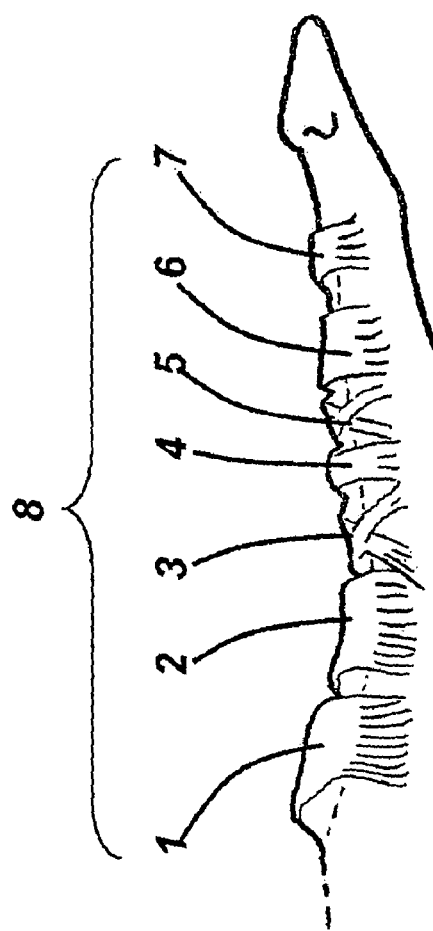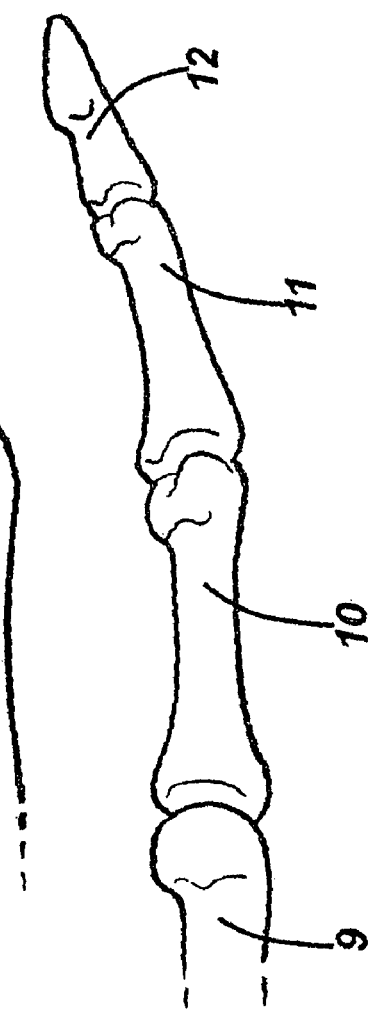

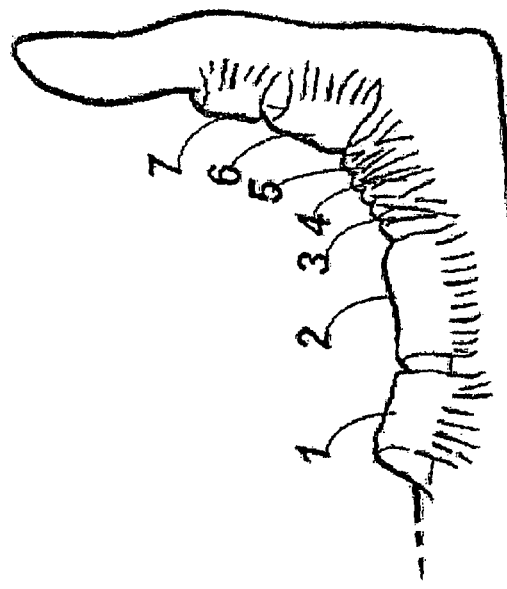
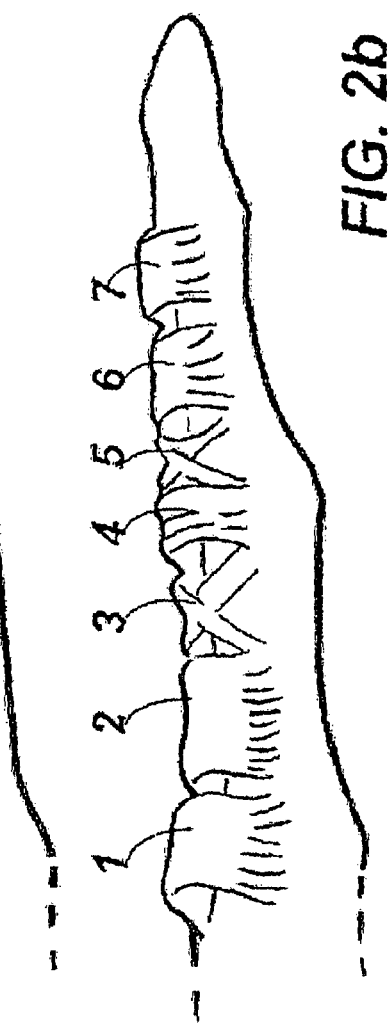
FIG. 2a
FIG. 2b

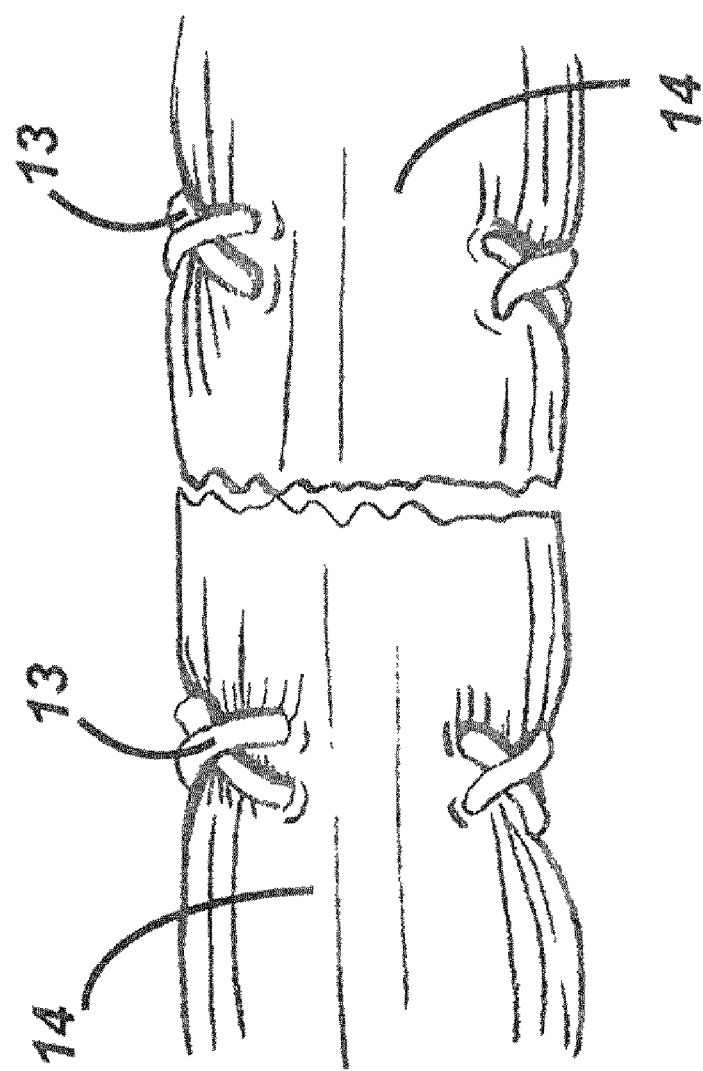

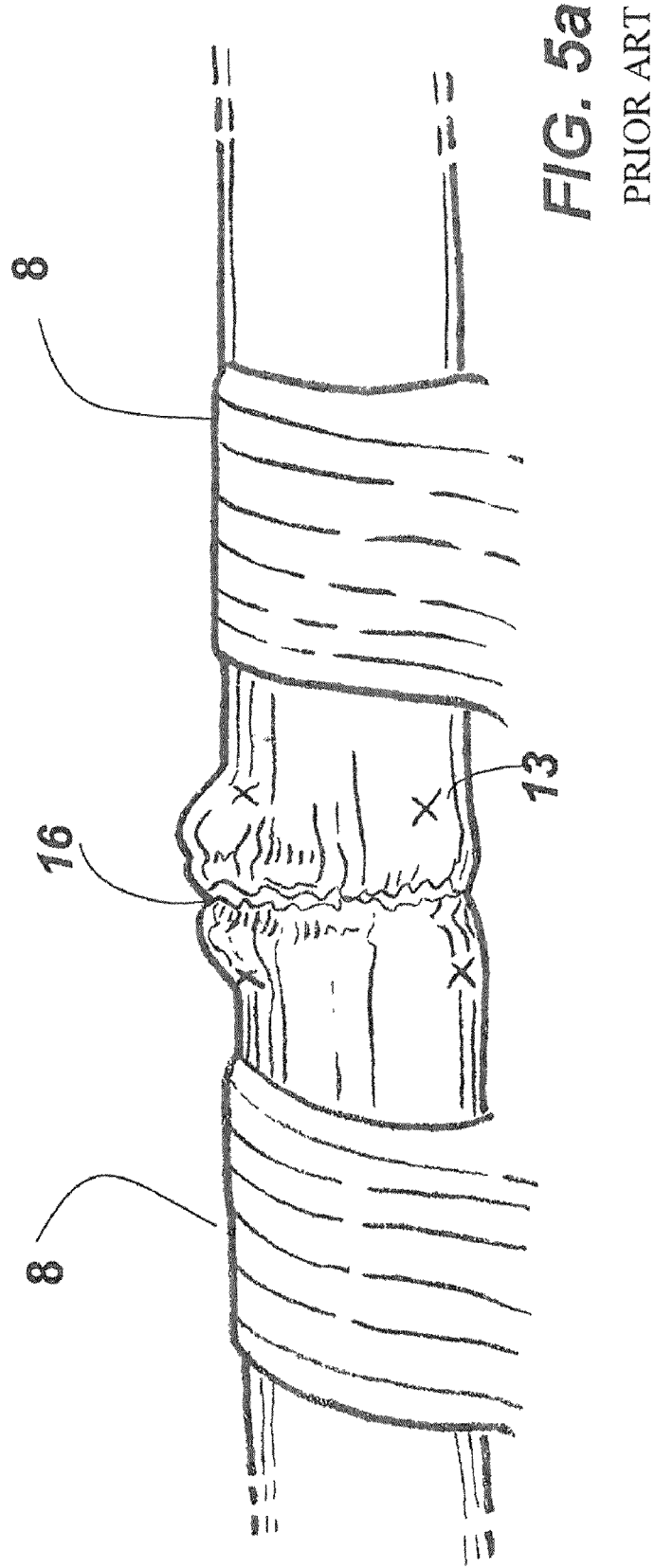

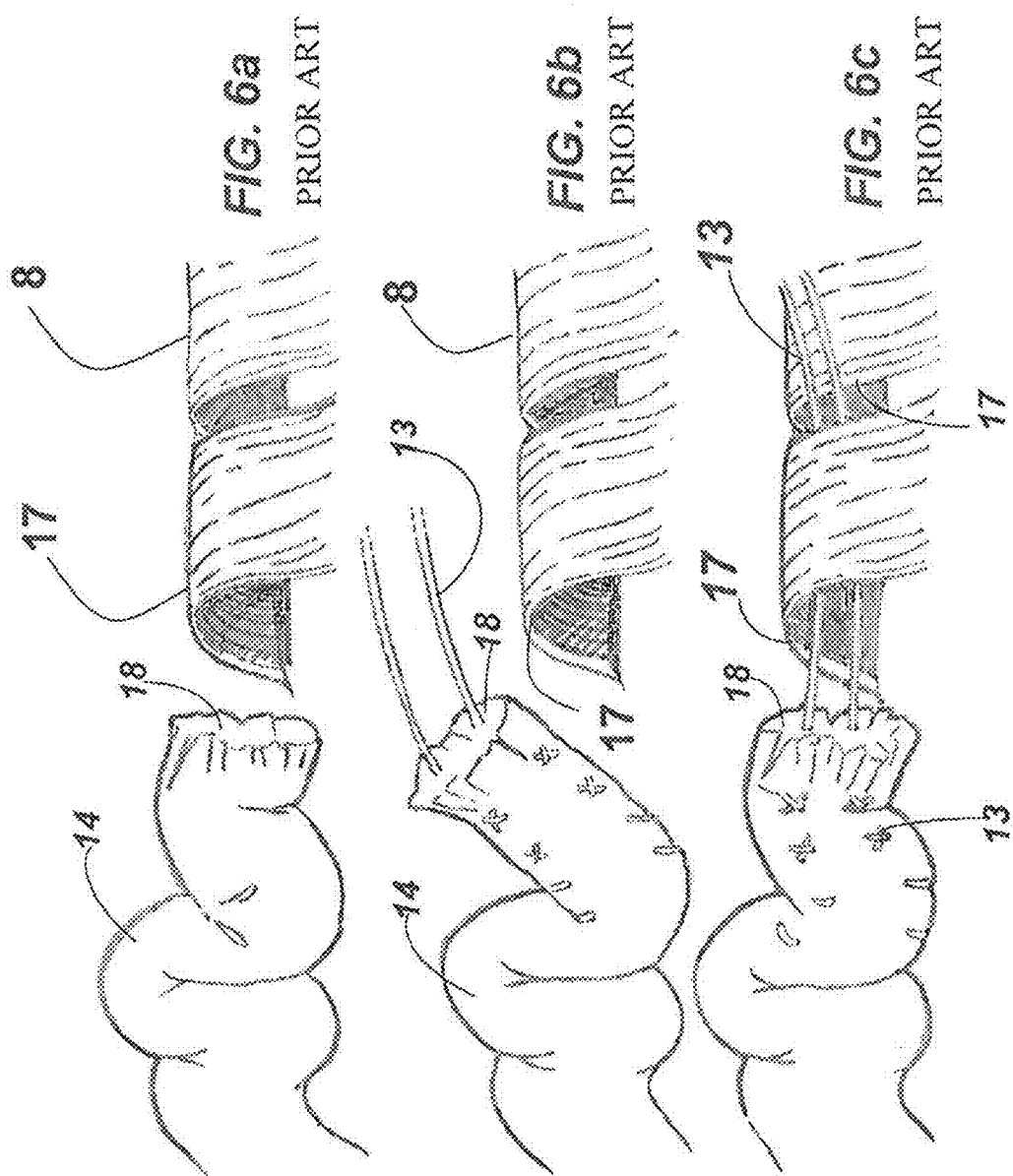

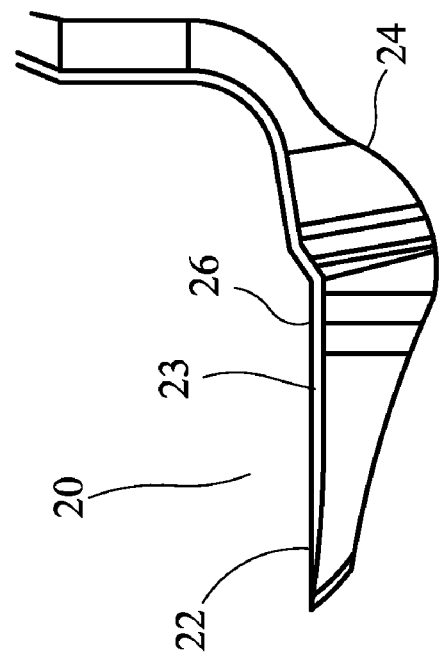
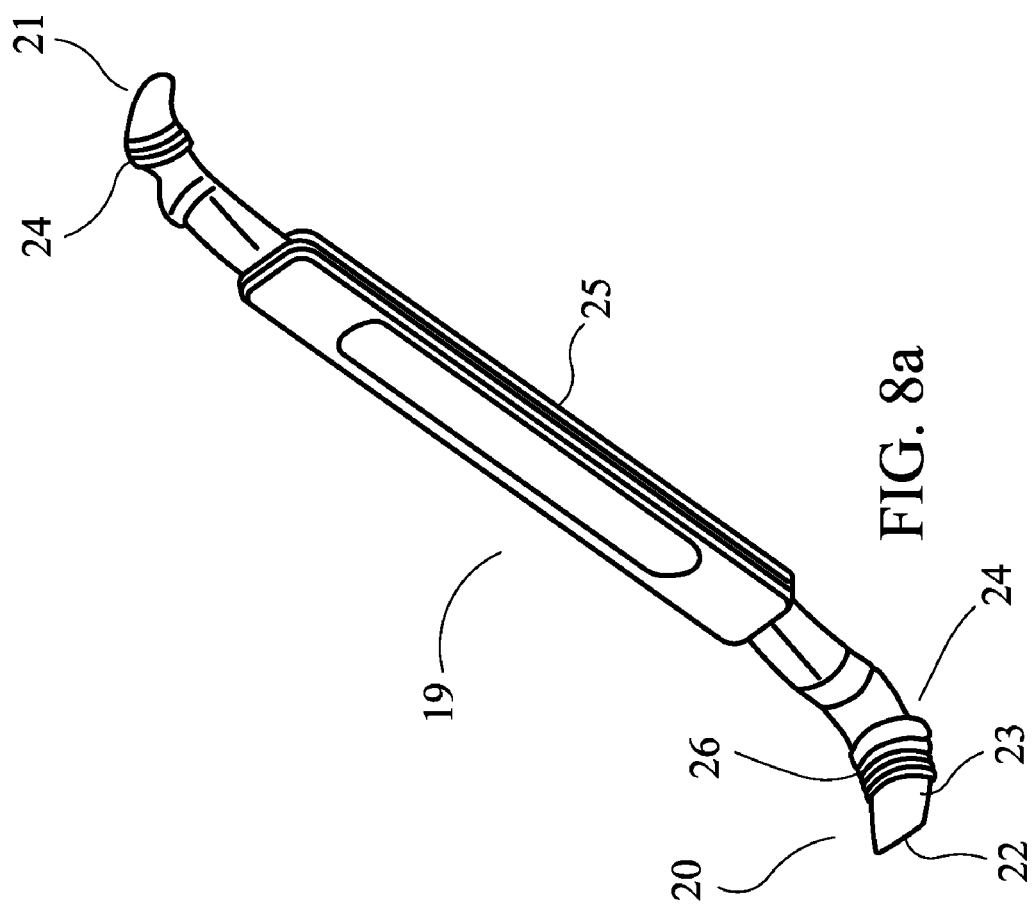

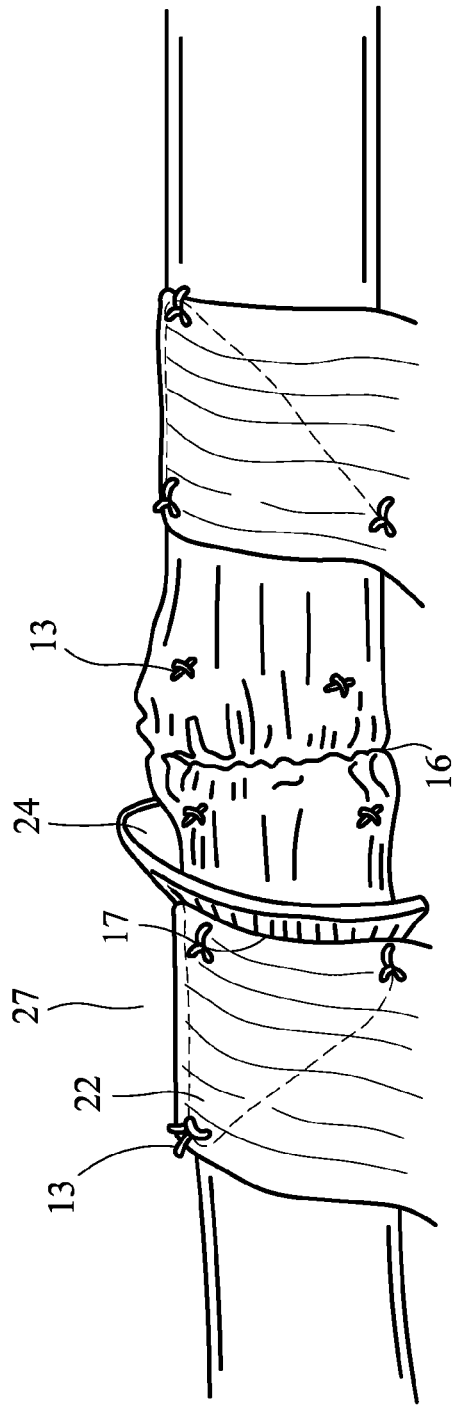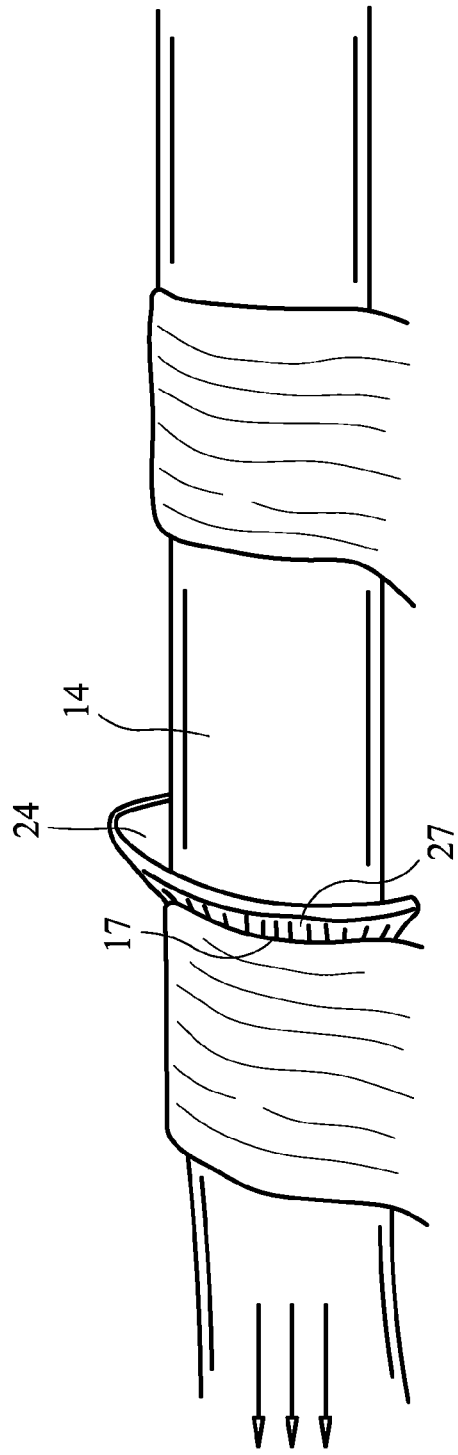

DEVICE AND METHOD FOR ASSISTING IN FLEXOR TENDON REPAIR AND REHABILITATION

CROSS REFERENCES TO RELATED APPLICATIONS

This application claims the benefit under 35 U.S.C. §119(e) of U.S. Provisional Application No. 60/955,729, filed on Aug. 14, 2007, the complete disclosure of which is incorporated herein by reference in its entirety.

FIELD OF THE INVENTION

The invention relates to a surgical device and method used to assist in the surgical repair and rehabilitation of damaged and/or severed tendons.

BACKGROUND OF THE INVENTION

In the hand, the fingers are moved by flexor and extensor tendons arising from muscles in the forearm. Inspection of the flexor tendon mechanism reveals three main components: 1) the skeleton, including the bones and the articulations or joints between the bones; 2) a tunnel or pulley system for the tendon; and 3) the tendon itself.

In each finger, two flexor tendons work to flex the proximal and distal interphalangeal joints, namely the flexor digitorum superficialis and the flexor digitorum profundis respectively.

A fibrous sheath holds the flexors tendons in close proximity to the phalanges of each finger to ensure that their pull produces immediate movement at the interphalangeal joint. In the absence of such a fibrous sheath, the flexor tendons simply "bow-string" and fail to produce the desired joint motion.

The flexor tendon sheath is highly specialized tissue that is anchored to bone and forms a very smooth but tight fibrous tunnel around the flexor tendon. With the flexor tendon surrounded by this flexor tendon sheath, there is a measurable hydrostatic pressure within the substance of the tendon. The flexor tendon sheath is not a uniform fibrous tunnel, but rather, is made of identifiable segments. The individual segments that make up the flexor tendon sheath are referred to as pulleys because of the mechanical role they play: holding the tendons close to the bone; preventing "bow-stringing" of the tendons; and ultimately translating the flexor tendon pull into joint motion.

For decades, surgical repair of severed tendons in the region of the hand containing the flexor tendon and the flexor tendon sheath has proven challenging and, to date, the results of such repairs are usually less optimal. For example, there are many current suture techniques designed for allowing the severed tendon ends to heal to each other while restoring the tensile strength of a tendon. Evidence gathered in connection with these various suturing techniques suggests that the number of suture strands and/or material across a tendon repair site directly correlates with the strength of the repair. In most situations, even when handling the tendon with the most delicate surgical techniques, the repair site ends up bulky and irregular. Thus, in contrast with the smooth and compact tendon located at the distal and proximal ends of the repair, most repair sites resemble bulky, irregular knots.

Given that the average repair site is often bulky or knotted, the repair site tends to abut the edges of the pulleys in the flexor tendon sheath, interfering with the tendon's ability to glide through its respective tendon sheath. Moreover, because the opening of a pulley does not expand to accommodate the bulk of the repair site, the edge of the pulley will often inflict significant damage to the repair site with every pass through the pulley, thereby impeding the tendon's ability to heal and adversely affecting the patient's overall post-operative recovery.

Repetitive injury to the repair site from the edge of a pulley may also contribute to the development of a "gap" across the repair site. Said "gap" consists of a premature separation of the sutured tendon edges, while the suture itself is still in continuity. Clinically, at this stage it may not be apparent that a rupture is imminent because the sutures are still holding. Nevertheless, the formation of a "gap" in the repair site will severely compromise the healing or it may simply make it impossible for the tendons to heal to each other. As a result, the suture eventually ruptures, at which point it becomes clinically evident that the repair has failed. In addition, rupture of the tendon repair can be caused by a combination of poor gliding of a bulky repair site and sufficient pull on the tendon during rehabilitation, or from patients who prematurely resume forceful activity that may exert a force in excess to what the repair site can withstand. Overly aggressive rehabilitation after flexor tendon repair surgery—which is intended to minimize stiffness—may also result in increased rated of tendon rupture.

Yet another very common and significant problem associated with tendon repair is the development of fibrosis and adhesions around the tendon and the repair site. Adhesions and fibrosis between the tendon repair site and the surrounding tissue is fostered by poor tendon gliding within the flexor tendon sheath during the healing process and results in finger stiffness and poor function. A second surgery referred to as "flexor tendon tenolysis" may be necessary to release the adhesions and fibrosis in order to improve finger motion. Tenolysis surgery is performed months after the original tendon repair surgery and is very demanding. Unfortunately, the results after tenolysis surgery are only moderately successful at best. Thus, patients who have had flexor tendon repair surgery face potentially significant complications either in the form of finger stiffness or tendon rupture before healing has occurred.

Yet another dilemma encountered in flexor tendon repair surgery is the tendency of an end of a flexor tendon to become inflamed and/or engorged after it has been severed, thereby making it difficult for the surgeon to direct and manipulate the tendon end through the flexor tendon sheath to a desired location. The situation is analogous to feeding the end of a frayed rope through the mouth of a pipe—only incalculably more delicate. Moreover, once the surgeon is able to direct the tendon end to a desired location, one or more inflamed and/or engorged severed tendon ends may further exacerbate the bulkiness and/or knottiness of the resulting repair site.

These, as well as other complex problems often associated with tendon repair, have led many surgeons to recognize flexor tendon repair surgery as one of the most difficult and challenging forms of surgery in the hand. Indeed, the surgical community often refers to the region of the hand containing the flexor tendons as "no man's land."

Accordingly, there is an existing demand for new and innovative flexor tendon repair techniques that will assist surgeons with, for example, facilitating the ability of a repair to glide through a flexor tendon sheath, while minimizing the amount of damage to the tendon that may be caused by excessive handling of the tendon during surgery when attempting to tunnel the cut end of a tendon through the pulleys of the flexor tendon sheath.

Several attempts have been made to help correct some of the problems associated with flexor tendon repair surgery. For example, U.S. Pat. Nos. 5,897,591 and 3,842,441 both disclose a temporary tubular implant which prevents the formation of post-operative fibrous adhesions between a repair site and its surrounding tissue. Furthermore, U.S. Pat. No. 7,112,221 discloses an implant which can be strapped around a bone, thus providing a prosthetic support which supplements the tendon sheath.

These and other references, however, do not address the problems that a surgeon often encounters when a repair site and/or tendon end is too bulky or inflamed to smoothly enter into one or more of the various pulleys in the flexor tendon sheath. Therefore, a device and method are desired that will assist a surgeon in directing a severed tendon end through the pulley system of its respective flexor tendon sheath to a desired location. More importantly, a device and method are desired that will facilitate the smooth gliding or passage of a repair site through its corresponding pulley system during tendon healing.

SUMMARY OF THE INVENTION

Most research demonstrating flexor tendon repair techniques has been done in vitro with cadaveric tendons removed from their respective flexor tendon sheaths. The focus of the majority of publications addressing flexor tendon repair is on the strength of repairs for various suture techniques or suture materials used in simulated, in vitro tendon lacerations. Therefore, current studies (the majority of which are in vitro) do not account for the interaction and resulting friction between a repaired flexor tendon and its respective, tightly-fitting flexor tendon sheath.

It is well known that the prognosis for a tendon repair is more predictable and generally better when the laceration to the tendon has taken place in a portion of the tendon that is not located within the flexor tendon sheath; for example, in the palm or the forearm. Conversely, the portion of the tendon within the flexor tendon sheath has acquired the name, "no man's land," because tendon repair surgery at this site can be very challenging and often has an unpredictable outcome. It is within this particular area, i.e., "no man's land," that the present invention has its preferred application.

It is an object of the present invention to provide a device and method that will facilitate the manipulation of a severed tendon end during surgery from its retracted position to a desired location through the several pulleys of the flexor tendon sheath.

Once the tendon is repaired using an accepted suture and repair technique, a significant amount of destructive rubbing and friction on the repair site will result as the repair site glides through and contacts the edges of the pulleys of the flexor tendon sheath. Therefore, it is a further object of the present invention to provide a device and method that will minimize the destructive rubbing and friction that a relatively bulky repair site experiences while passing or gliding through the tight pulleys of the flexor tendon sheath during rehabilitation.

Accordingly, one embodiment of the present invention is a non-implantable device comprised of a hollow member, preferably shaped as a partial funnel and/or cone, having an inner and outer surface, a flared mouth, and an elongated handle, preferably attached to the flared mouth, for ease of manipulation. In a preferred embodiment of the present invention, the hollow member is further comprised of a shaft and an apical end. During a flexor tendon repair procedure involving a severed tendon, the flared mouth of the hollow member is introduced into the pulley and placed directly adjacent to the free end of the tendon. The flared mouth of the hollow member creates a wider, artificial pulley edge that permits the inflamed tendon end to traverse the edge of the pulley while minimizing contact with the pulley as well as potential damage to the tendon. With the non-implantable device, an inflamed and/or engorged tendon end, that otherwise may not easily pass through the edge of a pulley, can be placed into the flared mouth of the device and gently compressed through the shaft and apical end of the device, wherein the tendon end will be simultaneously squeezed into the pulley in a smooth and non-damaging manner. The process is analogous to that of a shoehorn providing a smooth and gradual entry of a large heel into and through a sharp and tight edge of a shoe.

For example, after a suitable suture is placed on the free end of the severed tendon, the surgeon may then pull the tendon end through the flared mouth of the hollow member and into the shaft of the hollow member. Tension can then be applied on the suture so that the tendon end can be compressed and passed through the device and simultaneously through the pulley. The surgeon may continue to pull on the suture to deliver the free tendon end out of the pulley through its other end. The process of passing the tendon through a pulley can be repeated through other pulleys as many times as necessary until the tendon end reaches the desired site of repair, wherein the surgeon can then suture the tendon end to the other free tendon end using one of the many validated suture techniques currently accepted and practiced.

Another embodiment of the present invention is an implantable device also comprised of a hollow member, preferably shaped as a partial funnel and/or cone, having an inner and outer surface and a flared mouth. In a preferred embodiment, the hollow member is further comprised of a shaft and an apical end. The implantable device may also include a detachable, elongated handle which would allow the surgeon to manipulate the implantable device into a desired location. The device can also be made of a material capable of being sutured to the pulley's fibrous tissue.

The implantable device can remain in the patient's hand after completion of a flexor tendon repair surgery, and can also be made of a safe, biodegradable material which is known, accepted, and currently used in surgical procedures. Alternatively, the implantable device can be made of a non-biodegradable material, and removed from the patient's hand at a later date when the suture site has sufficiently healed. The undersurface of the implantable device, that is the surface of the device that comes in direct contact with the tendon, can also be lubricated with any number of biocompatible lubricants.

In circumstances wherein the repair site must glide into and out of a single pulley edge during finger flexion, the surgeon can place the apical end of the implantable device into the pulley edge so that the flared mouth of the device sits directly adjacent to the repair site, thus allowing the repair site to smoothly glide into and out of the implantable device and corresponding pulley. With the implantable device in place, the surgeon can insure that during finger flexion a bulky repair site will smoothly glide in and out of one or more pulleys without abutting the pulley edges, thus minimizing the damage caused to the repair site and minimizing the possibility of tendon rupture. With improved tendon gliding, the implantable device also minimizes the formation of adhesions around the tendon and improves finger motion; the need for a future secondary operation to remove adhesions around a repair site is also obviated.

In another embodiment, wherein the repair site must glide partially into a more proximal pulley and partially into a more distal pulley during flexion, the surgeon can insert one implantable device into the edge of the pulley proximally adjacent to the repair site, and another implantable device into the edge of the pulley distally adjacent to the repair site. The respective flared mouths of each device would each face the repair site as well as one another. Utilizing the foregoing arrangement, the surgeon can ensure that a bulky repair site smoothly glides into and out of a proximal and distal pulley edge.

In another embodiment of the implantable device, the implantable device is comprised of a hollow member, preferably shaped as a cylindrical tube or barrel cut in half along its longitudinal axis, having an inner and outer surface, a shaft, and two flared mouths, one at each end of the shaft. By suturing this double-ended implantable device into a pulley so that the shaft of the device completely traverses the underside of the pulley and each of the device's flared mouths is positioned at the pulley's proximal and distal edges, a surgeon can facilitate the gliding of a repair site through the entire length of a pulley. During finger flexion the repair site would enter the proximal or distal end of the pulley through one of the flared mouths of the double-ended implantable device; traverse the shaft of the device; exit and reenter the pulley through the other flared mouth of the device; re-traverse the shaft of the device; and exit the pulley through the same flared mouth that had first served as an entrance to the pulley. The double-ended implantable device can also be sutured to the periosteum of the anterolateral and anteromedial ridges of the corresponding phalanx, or alternatively affixed with small screws to the bone, where it can be used to repair or reconstruct a pulley.

BRIEF DESCRIPTION OF THE DRAWINGS

FIG. 1a is a lateral view of the flexor tendon sheath, identifying each reinforced pulley of the flexor tendon sheath's pulley system. FIG. 1b is a lateral view of the metacarpal, the proximal phalanx, the middle phalanx, and the distal phalanx.

FIG. 2a is a lateral view of the flexor tendon sheath when the finger is flexed, and FIG. 2b is a lateral view of the flexor tendon sheath when the finger is extended.

FIG. 4 is a view of severed tendon ends sutured together with a "locking" suture technique.

FIG. 5a is a view of a bulky repair site in between two pulleys.

FIG. 6a is a view of a retracted free end of a severed tendon. FIG. 6b is a view of the retracted free end of a severed tendon sutured with a suitable technique. FIG. 6c is a view of a sutured tendon end ready to be passed through an adjacent pulley.

FIG. 8a is a view of a non-implantable embodiment of the present invention. FIG. 8b is a cross-sectional view of the non-implantable embodiment of the present invention.

FIG. 11a is a view of a bulky repair site adjacent to a pulley with an implantable device sutured to the underside of the pulley. FIG. 11b is a view of a bulky repair site gliding into an adjacent pulley with an implantable device sutured to the underside of the pulley.

DETAILED DESCRIPTION OF THE PREFERRED EMBODIMENTS

Figure 3A:
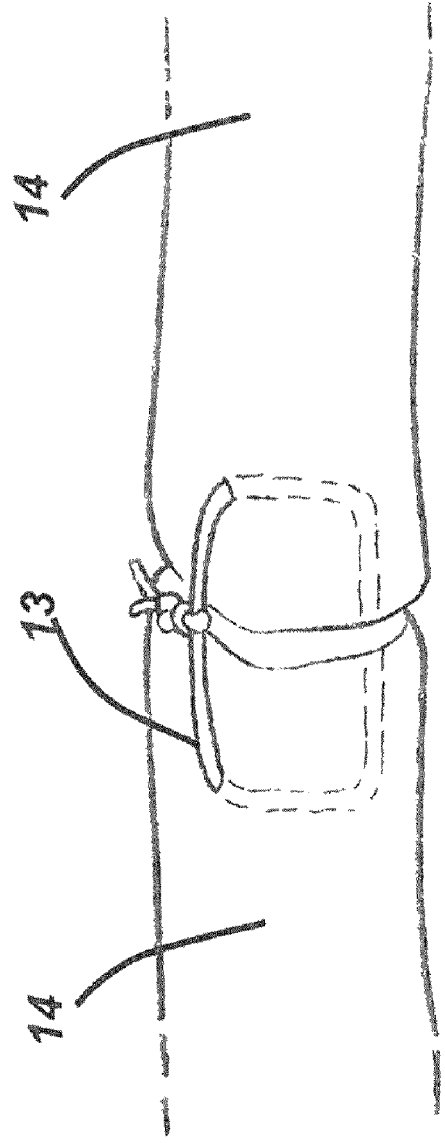
FIG. 3a is a view of severed tendons sutured together with a simple stitch.

FIG. 1a illustrates the specific segments of a flexor tendon sheath 8 that are critical for the proper function and effectuation of finger flexion. FIG. 1b further illustrates a finger, its skeleton, and the different finger joints associated with the flexor tendon sheath 8. Pursuant to proper anatomic nomenclature, wherein structures closer to the head are referred to as "proximal" and structures further from the head are referred to as "distal," FIG. 1b depicts the metacarpal 9, the proximal phalanx 10, the middle phalanx 11, and the distal phalanx 12.

As depicted in FIG. 1a, the flexor tendon sheath 8 is a continuous pulley system starting with the most proximal pulley 1 and finishing with the most distal pulley 7. The system of pulleys that comprises the flexor tendon sheath 8 has identifiable reinforced segments which form and correspond to each individual pulley, 1,2,3,4,5,6 and 7.

As illustrated in FIGS. 2a and 2b, the criss-cross arrangement of fibres in pulleys 3 and 5, located near the interphalangeal joints, are connected via a flimsy collapsible tissue that allow pulleys 3 and 5 to collapse when the finger flexes. Pulleys, 1, 2 and 6, are made of a thicker, non-collapsible tissue, and thus, remain unchanged during finger flexion. The non-collapsible thicker pulleys, 1, 2 and 6, are imperative for the proper mechanical function of the flexor mechanism in the finger, and whenever damaged and/or missing, must be repaired or reconstructed.

In addition to the skeletal structure and pulley system, the flexor tendon mechanism is further comprised of the tendon itself. Tendon tissue is comprised of a longitudinal array of collagen fibers within a surrounding matrix. The outer surface of the tendon is glistening smooth for proper gliding within a respective pulley. While tendon tissue is very dense, it is also very delicate and easily damaged when handled during surgery. The tendon's longitudinal array of fibers causes the tendon to easily split lengthwise, thus making suturing a severed tendon a rather difficult procedure.

Figure 3B:
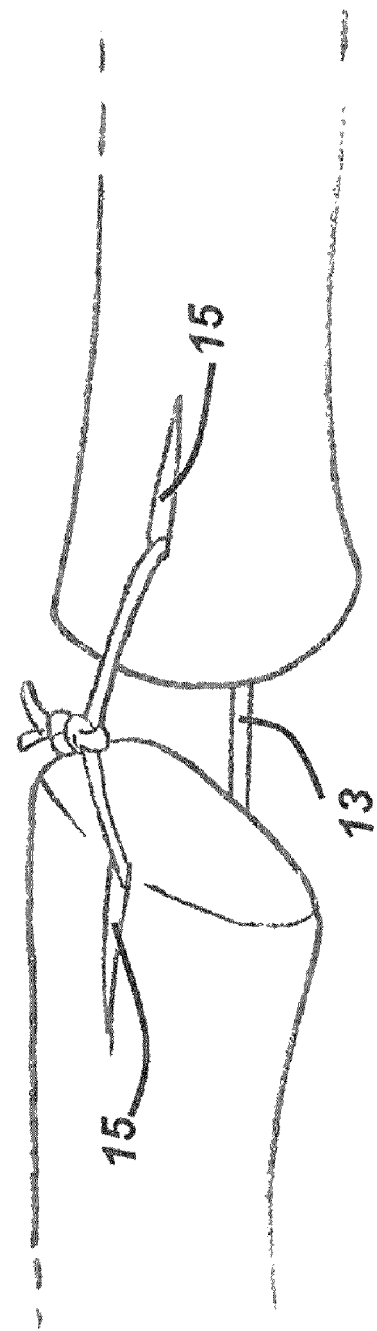
FIG. 3b is a view of simple suture stitch splitting the tendon tissue lengthwise.

FIGS. 3a and 3b illustrate how a simple suture 13 is generally an unacceptable technique for suturing a severed tendon 14 because of a tendency to cause a lengthwise split and/or tear 15 in the tendon tissue when tension is exerted on the repair site. To avoid splitting the delicate tendon tissue, many techniques for repair of a severed tendon have been proposed, including a favored technique, as shown in FIG. 4, wherein the suture 13 is "locked" to itself in order to provide a strong grip on the tendon tissue, thus minimizing the potential for tearing or splitting.

As illustrated in FIG. 5a, however, in spite of their ability to minimize longitudinal tearing and/or splitting of the tendon, suture techniques such as the "locking" technique often result in bulky and/or knotted repair sites 16 that abut with the flexor tendon sheath's pulley system, thus impairing the tendon's ability to smoothly glide through the flexor tendon sheath 8, as well as causing extensive damage to the repair site 16 itself.

Figure 5B:
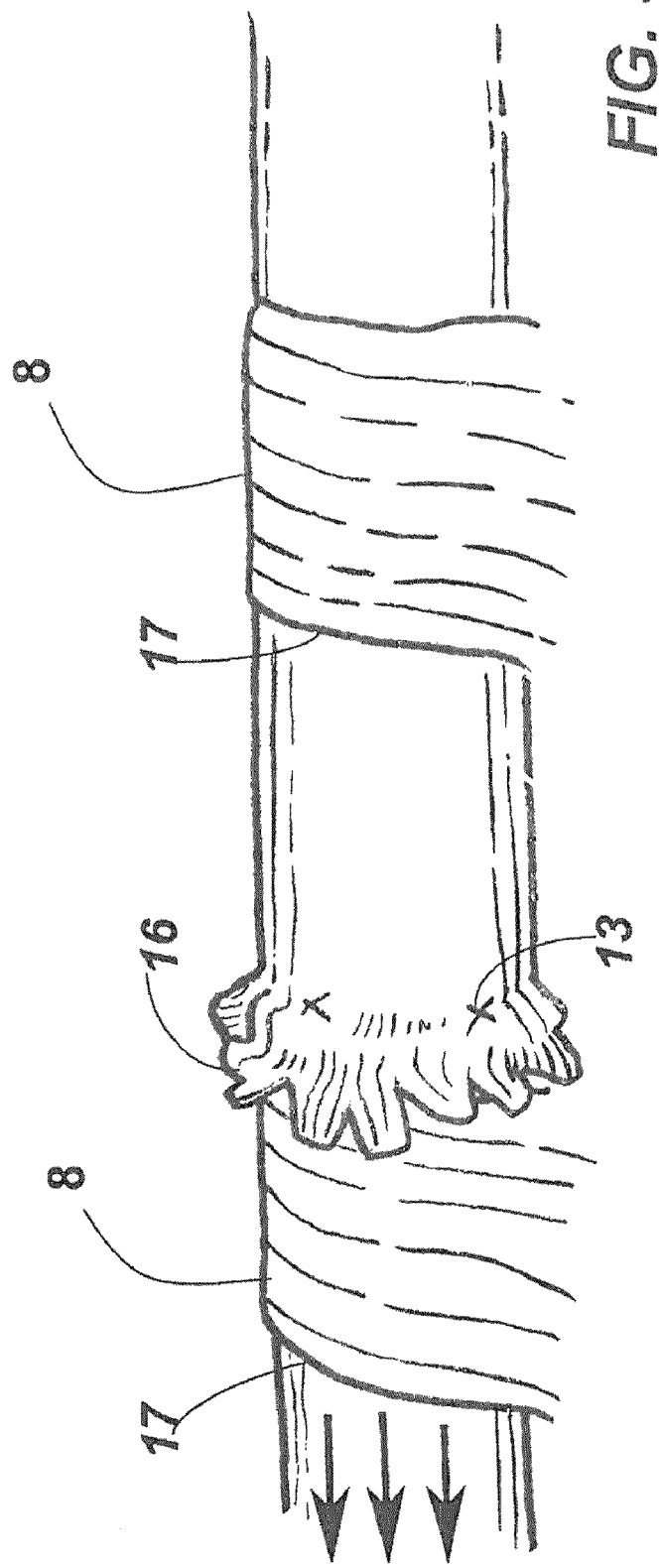
FIG. 5b is a view of a bulky repair site abutting the edge of a pulley as the tendon repair site moves during finger flexion.
Figure 5C:
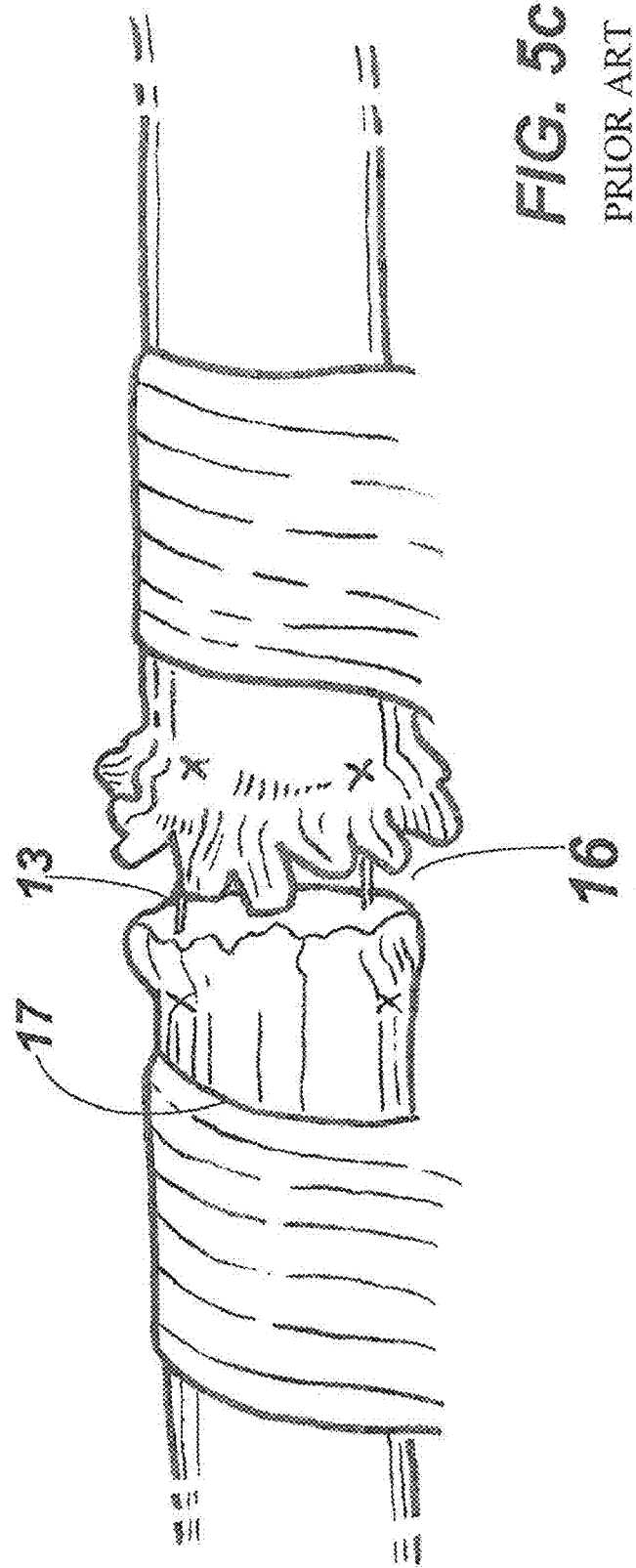
FIG. 5c is a view of a damaged repair site after it has abutted the edge of a pulley during finger flexion.

As illustrated in FIG. 5b, a bulky repair site 16 can abut with the edge of a pulley 17 as the tendon glides through the flexor tendon sheath 8 during finger flexion. The edge of the pulley 17 can significantly damage a repair site 16. As illustrated in FIG. 5c, the damage to the repair site 16 can be so extensive that the previously sutured tendon ends may once again separate. Although some existing suture techniques, such as an epitendinous repair, can minimize the amount of separation, they do not eliminate the problem. Thus, damage caused to a repair site as a result of unwanted abrasions between a bulky repair site and an adjacent pulley edge remains a major concern in flexor tendon repair surgery.

Similar problems may also arise when the tendon 14 is severed and retracts proximally into the palm. As illustrated in FIGS. 6a and 6b, when a severed tendon 14 retracts from the flexor tendon sheath, the surgeon must find the free tendon end 18; place a proper suture 13 on the free tendon end; and deliver it to a desired location where it will be sutured to the other free tendon end. As illustrated in FIG. 6c, this particular procedure requires passing the sutured free tendon end 18 through one or more pulley edges 17 in the flexor tendon sheath 8.

Figure 7A:
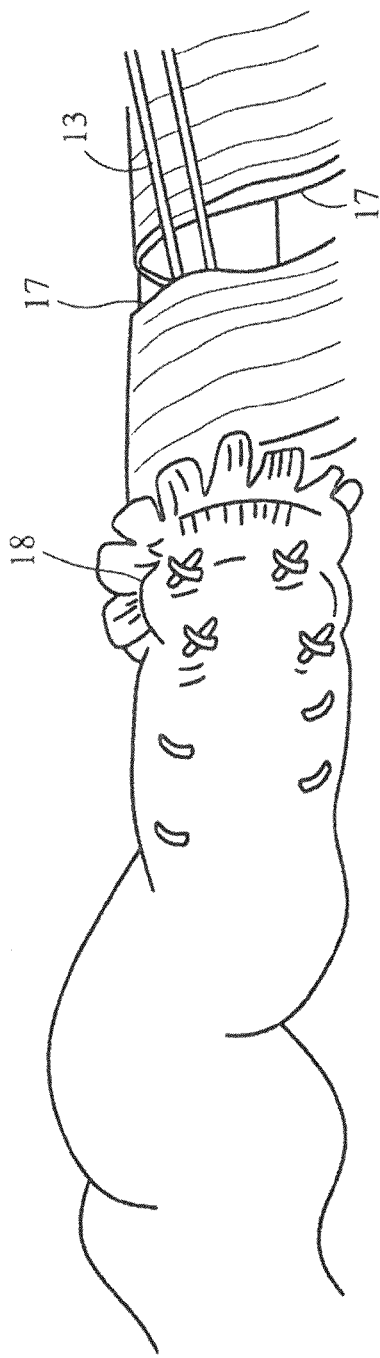
FIG. 7a is a view of a sutured tendon end being forced into a pulley and abutting the edge of the pulley.
Figure 7B:
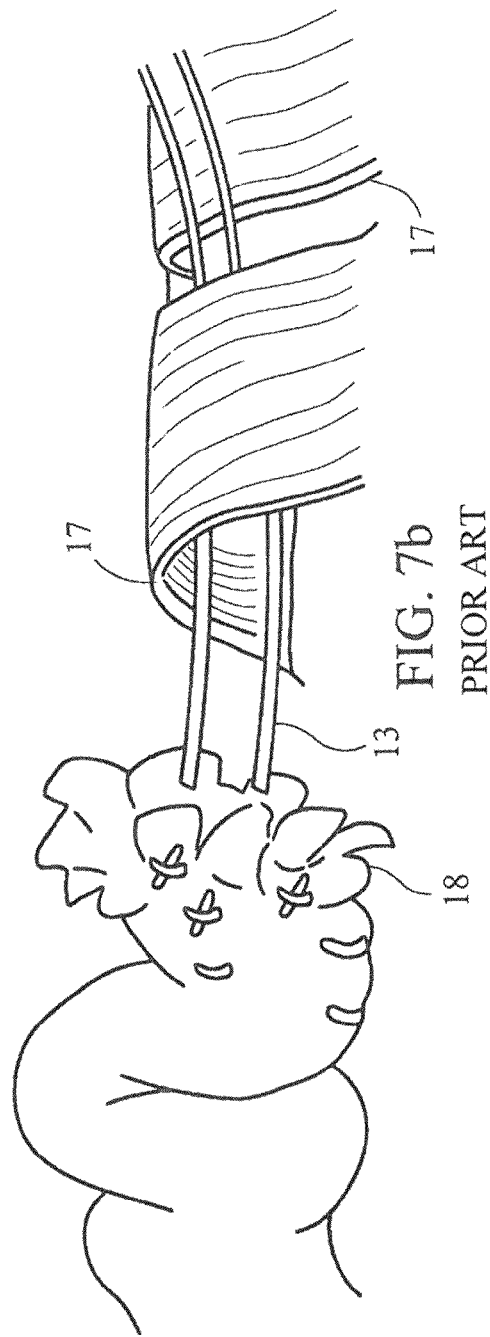
FIG. 7b is a view of a damaged tendon end after an unsuccessful attempt at forcing the tendon end into an adjacent pulley.

However, unlike most depictions found in today's relevant medical literature, and unlike the cadaveric tendons severed and utilized in many in vitro procedures, a tendon end tends to become inflamed and/or engorged after it has been severed or lacerated in vivo. As depicted in FIG. 7a, an inflamed or engorged tendon end 18 considerably hinders a surgeon's ability to pass the free tendon end 18 through the flexor tendon sheath because of its tendency to abut any one of the several pulley edges 17 in the flexor tendon sheath. As illustrated in FIG. 7b, forcing an inflamed and/or engorged free tendon end 18 through a pulley edge 17 can result in significant abrasion and damage to the free tendon end 18.

The present invention utilizes certain tendon properties to overcome the foregoing problems. The tendon itself is compressible in the sense that its cross-sectional area can be minimized when it is compressed circumferentially. When compressed, the fluid within the tendon is simply pushed to the surrounding non-compressed tissue. On the other hand, the tendon is not very elastic lengthwise—it behaves more like a tight rope than a bungee cord. Accordingly, the present invention provides a device and method that facilitates and negotiates the passage of an inflamed tendon end or a bulky repair site through the edge of a tendon pulley by enlarging the space within which the tendon end or repair site can enter a pulley while minimizing the volume of the inflamed tendon end or bulky repair site by redistributing the tendon's fluid content with light compression.

In one embodiment of the present invention, a non-implantable device 19 is utilized to assist the surgeon with the passage of a free tendon end 18 through various pulleys in the flexor tendon sheath 8 to a repair site. As illustrated in FIGS. 8a and 8b, the non-implantable device 19 includes a hollow member 20, preferably shaped as a partial or half funnel and/or cone, having an inner and outer surface, a flared mouth 24 and an elongated handle 25 for ease of manipulation. While the flared mouth 24 is preferably shaped as a flat arc with an upward and outwardly protruding edge, any shape is acceptable so long as the flared mouth facilitates the passage and/or gliding of a tendon end or repair site through the tendon sheath. In a preferred embodiment of the present invention, the hollow member 20 is further comprised of a shaft 23 and an apical end 22. In another embodiment, the non-implantable device 19 includes a second hollow member 21 of smaller proportions which can be utilized in smaller patients or smaller pulleys, 5, 6, and 7. In yet another embodiment, the hollow member, 20 and 21, of the non-implantable device further includes a graded scale 26 on the outer surface of the shaft 23 of the hollow member, wherein the scale 26 serves as a measuring tool to assist the surgeon in determining the extent to which the device can be inserted into a flexor tendon sheath. In yet another embodiment, the inside of the shaft 23 of the non-implantable device 19 can be coated or lubricated with a non-hazardous, slick material that would minimize resistance between the shaft 23 of the device and the tendon end 18.

With the non-implantable device 19, an inflamed and/or engorged severed tendon end 18 can be fed into the flared mouth 24 of the non-implantable device 19 and gently pulled and compressed through the shaft 23 and apical end 22 of the device, wherein the tendon end will be simultaneously compressed into and through a pulley edge 17 in a smooth and non-damaging manner. The tendon end can then be passed through the pulley, and delivered to the other edge of the pulley wherein the tendon end can be pulled out of the pulley. The procedure can be repeated as many times as necessary until the tendon end reaches a desired location, at which time the surgeon can then repair the tendon using one of the many suture techniques currently accepted and practiced.

Figure 9A:
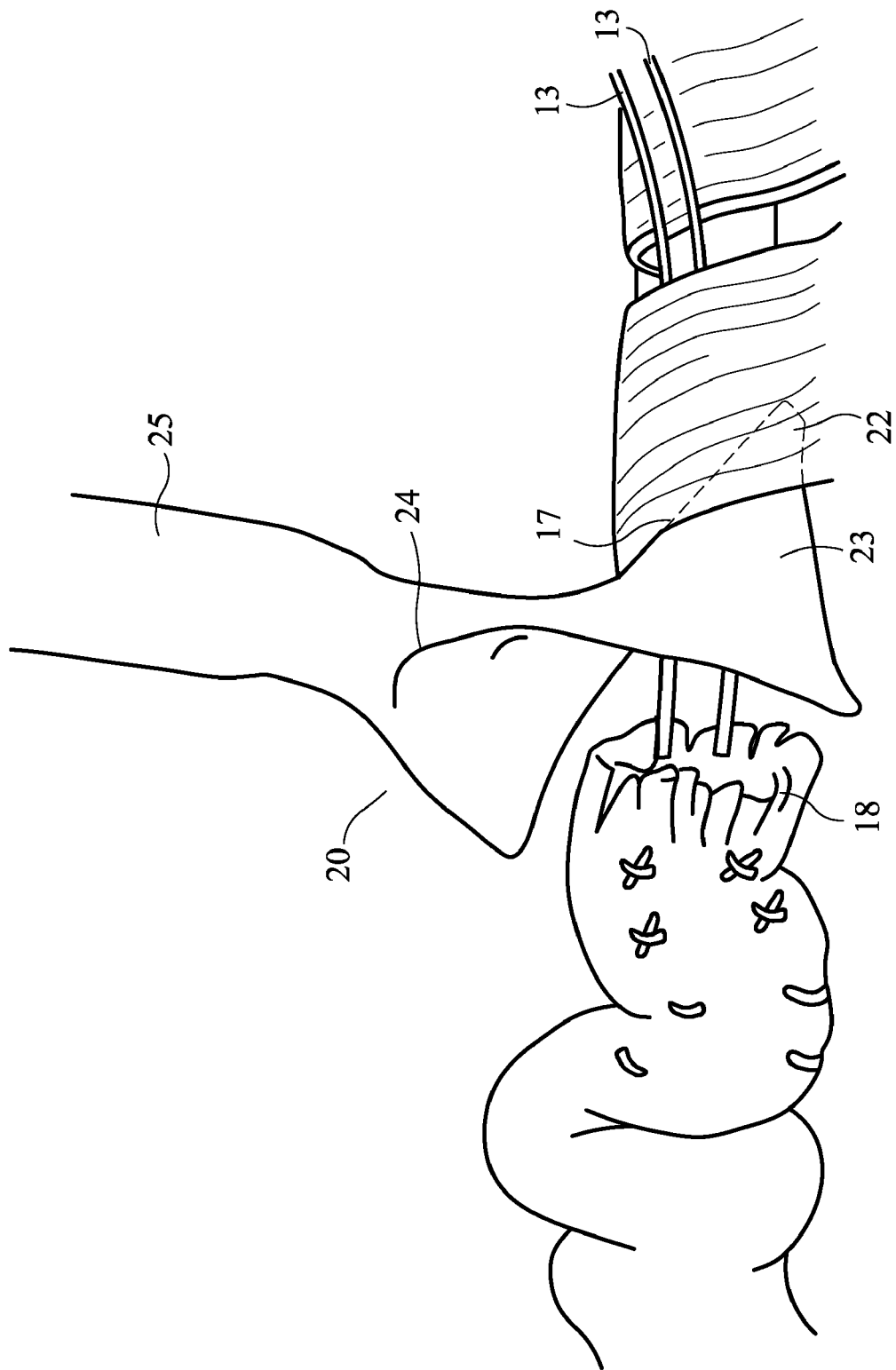
FIG. 9a is a view of the hollow member of the non-implantable device just before it is inserted into a pulley.
Figure 9B:
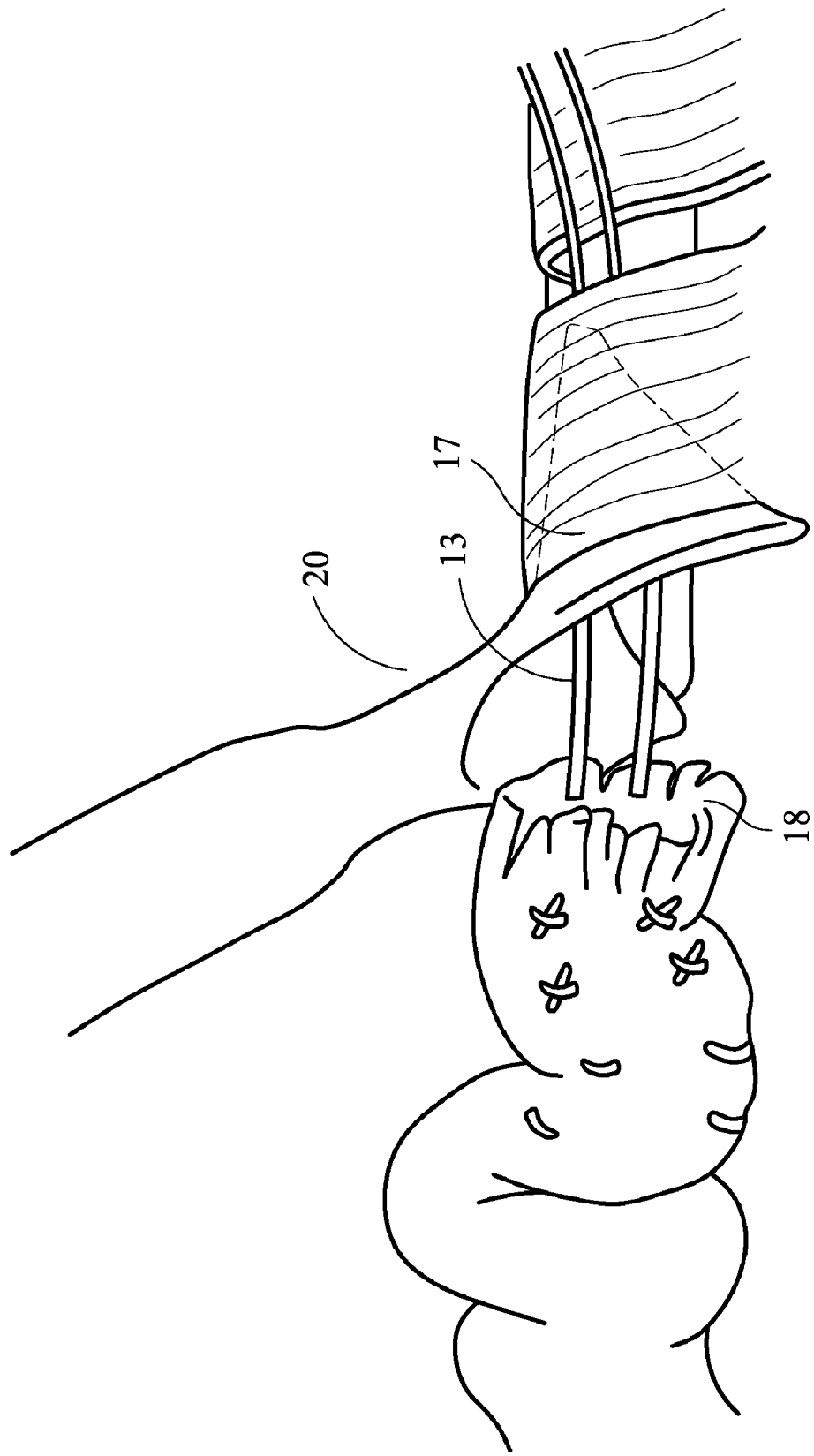
FIG. 9b is a view of the apical end of the hollow member of the non-implantable device being inserted into the edge of a pulley.
Figure 9C:
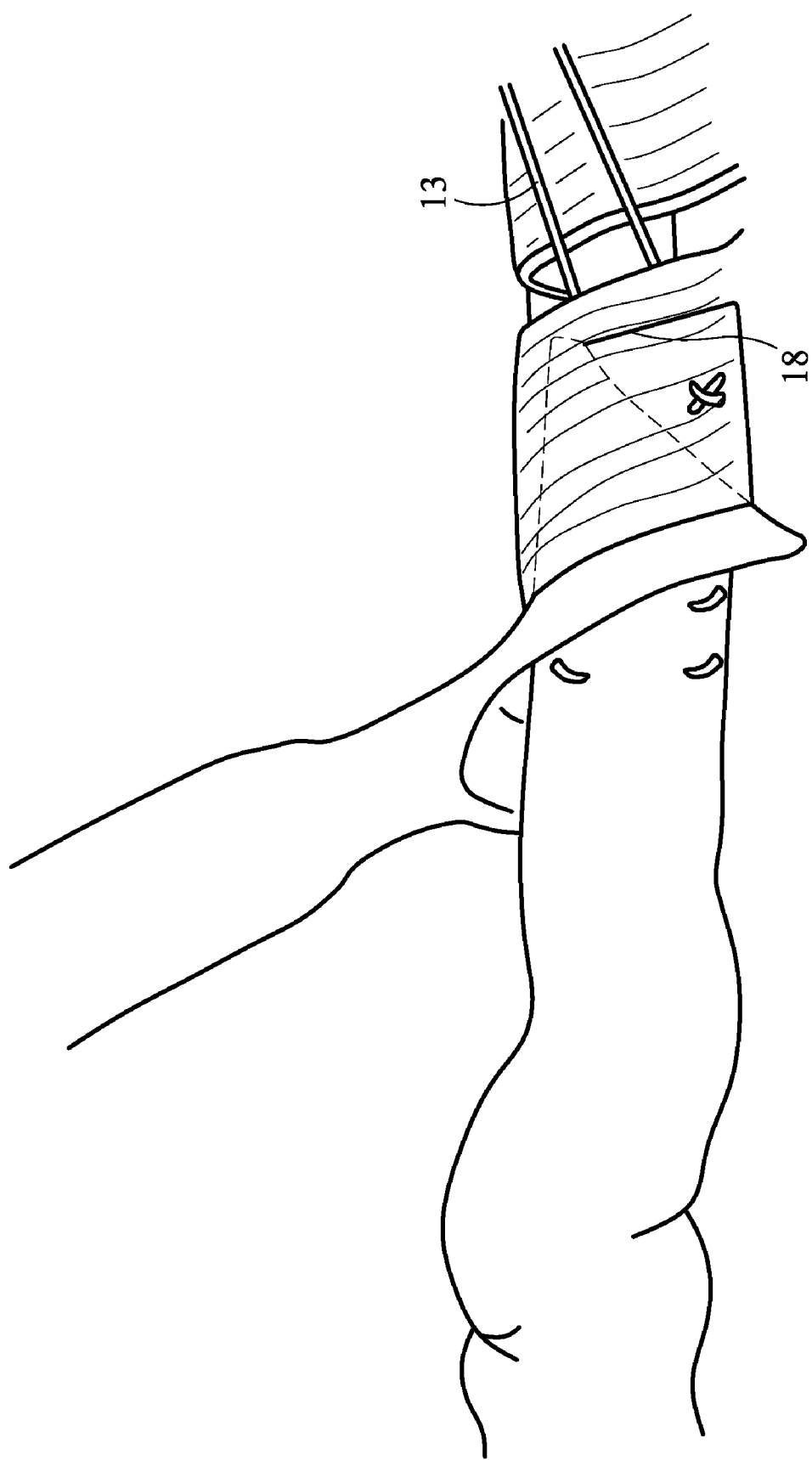
FIG. 9c is a view of a sutured tendon end being fed into the flared mouth of the hollow member of the non-implantable device, and simultaneously passed through the apical end of the hollow member of the non-implantable funnel device and edge of an adjacent pulley.

For example, as illustrated in FIG. 9a, during a flexor tendon repair procedure, the hollow member 20 of the non-implantable device 19 is introduced into the edge of a pulley 17 with the assistance of the handle 25. Preferably, the apical end 22 of the hollow member 20 is introduced into the pulley, while the flared mouth 24 of the hollow member 20 is placed directly adjacent to the tendon end 18 so that it faces the free end of the tendon. As illustrated in FIG. 9b, a suture 13 previously placed on the free end of the severed tendon 18 is then simultaneously passed through the hollow member 20 of the non-implantable device 19 and the edge of the pulley 17. As illustrated in FIG. 9c, tension is then applied on the suture 13, thereby pulling the free tendon end 18 into and through the pulley, wherein the procedure can be repeated if desired.

Figure 10:
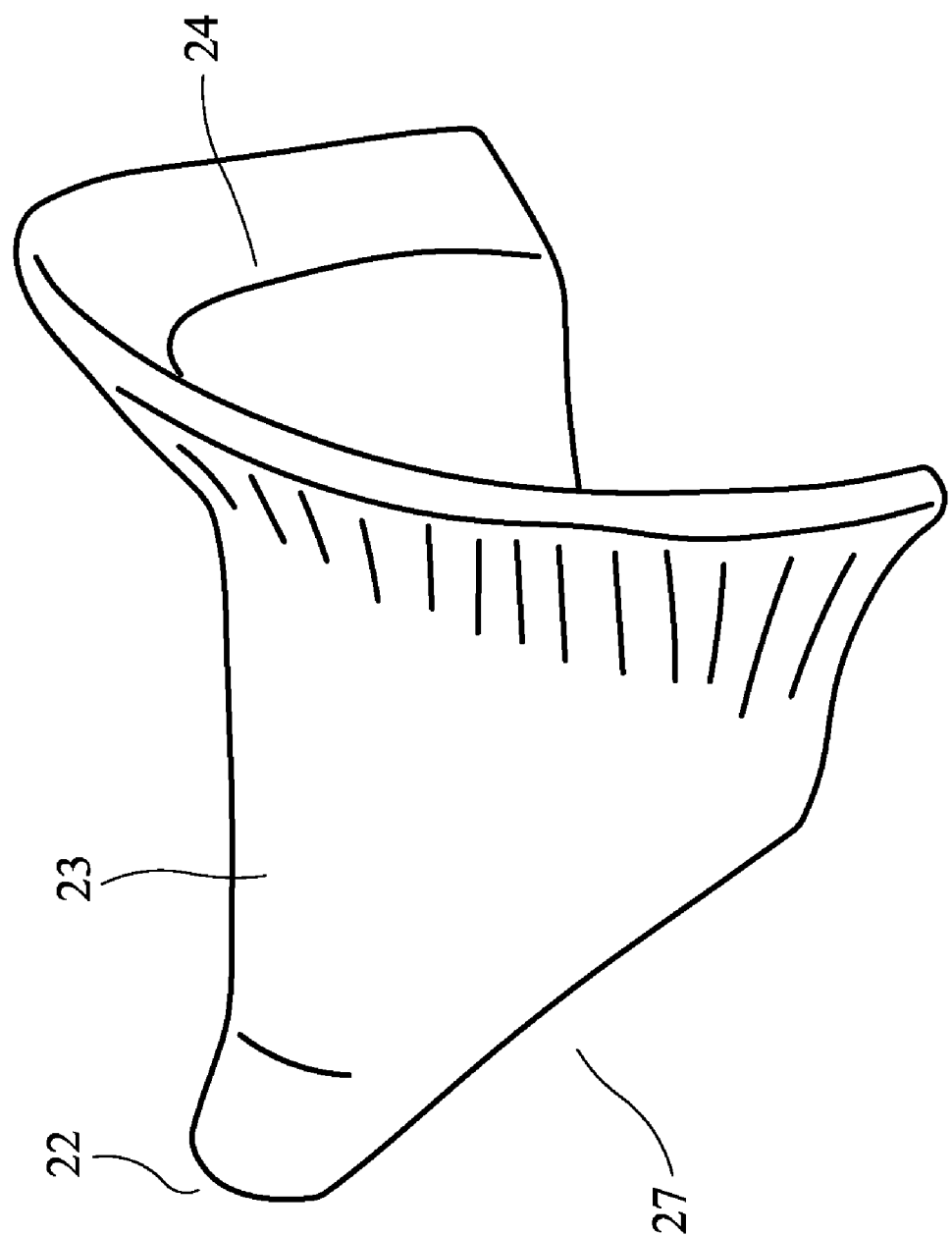
FIG. 10 is a lateral view of an implantable embodiment of the present invention.

Another embodiment of the present invention is an implantable device 27 which can remain in the patient's hand after the completion of a flexor tendon repair surgery. As illustrated in FIG. 10, the implantable device 27 includes a hollow member, preferably shaped as a partial funnel and/or cone, having an inner and outer surface and a flared mouth 24. As depicted in FIG. 10, the inner surface is at least in part concave, and the outer surface is at least in part convex. While the flared mouth 24 is preferably shaped as a flat arc with an upward and outwardly protruding edge, any shape is acceptable so long as the flared mouth facilitates the passage and/or gliding of a tendon end or repair site through the tendon sheath. As depicted in FIG. 10, the flared mouth 24 is at least in part arcuate.

With reference to FIG. 10, the inner surface, the outer surface, and the flared mouth 24 of the implantable device 27 are at least partially arcuate in cross section in planes parallel to the width of the implantable device 27. Furthermore, with reference to FIGS. 10-11e, the inner surface, the outer surface, and the flared mouth 24 are at least partially arcuate in cross section in planes transverse to the direction of passage of the tendon end or repair site.

In a preferred embodiment of the present invention, the hollow member 20 is further comprised of a shaft 23 and an apical end 22. As depicted in FIG. 10, the shaft 23 is also at least partially arcuate in cross section in a plane parallel to the width of the implantable device 27, and, as depicted in FIGS. 10-11e, the shaft 23 is also at least partially arcuate in cross section in a plane transverse to the direction of passage of the tendon end or repair site. The implantable funnel device 27 can be made of a safe, biodegradable material which is known, accepted, and currently used in surgical procedures.

Alternatively, the implantable device 27 can be made of a non-biodegradable material, and can be removed from the patient at a later date when the suture site has sufficiently healed. In another embodiment, the outer surface of the shaft 23 of the hollow member of the implantable device, 27, further includes a graded scale 26, wherein the scale 26 serves as a measuring tool to assist the surgeon in determining the extent to which the device can be inserted into a flexor tendon sheath. In another embodiment, the implantable device 27 may also include a detachable, elongated handle attached to the shaft which would allow the surgeon to manipulate the device into a desired location. In yet another embodiment the inside of the shaft 23 of the implantable device can be coated or lubricated with a non-hazardous, slick material that would minimize any resistance between the shaft 23 of the device and the repair site, thereby improving the tendon's gliding function. The size of the implantable device will vary in accordance with the size of the patient's particular flexor tendon sheath and pulley system.

The implantable device 27 can be utilized to assist a bulky repair site 16 glide in an out of one or more pulley edges 17 during flexion, while minimizing damage to the repair site as a result of excessive contact or abrasion with a pulley edge. For example, as illustrated in FIG. 11a, the repair site 16 must glide into and out of a single pulley edge 17 during flexion. To assist the tendon, the apical end 22 of the implantable device 27 is first introduced into the pulley edge 17 so that the flared mouth 24 lies directly adjacent to the repair site 16, thus facing the repair site. When the implantable device 27 is satisfactorily placed into the pulley, the implantable device can then be sutured to the fibrous tissue on the undersurface of the pulley. As illustrated in FIG. 11b, during finger flexion the repair site 16 enters the flared mouth 24 of the implantable device 27. The repair site 16 is then gently compressed as it traverses through the shaft 23 and through the apical end 22 of the implantable device 27, thereby allowing the repair site 16 to simultaneously glide in and out of the pulley edge 17 with minimum contact or abrasion.

Figure 11C:
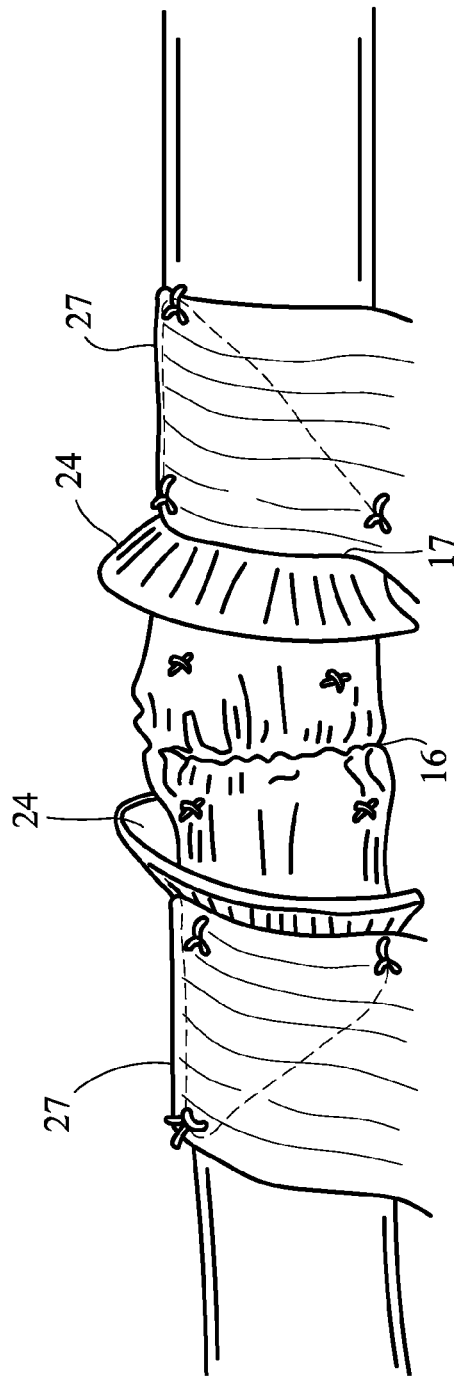
FIGS. 11c, 11d, and 11e are views of a bulky repair site gliding into a distally adjacent and proximally adjacent pulley.
Figure 11D:
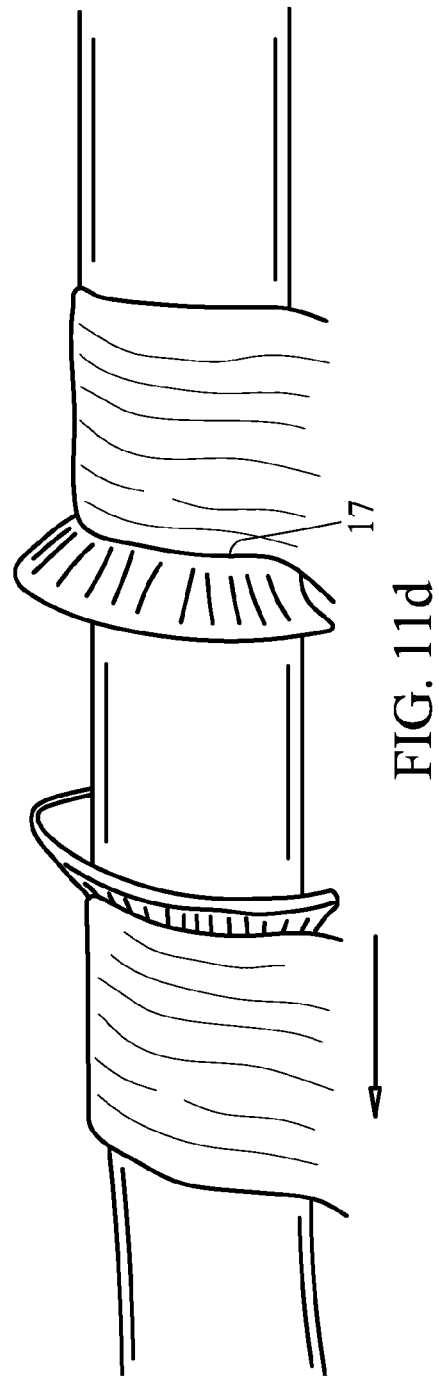
Figure 11E:
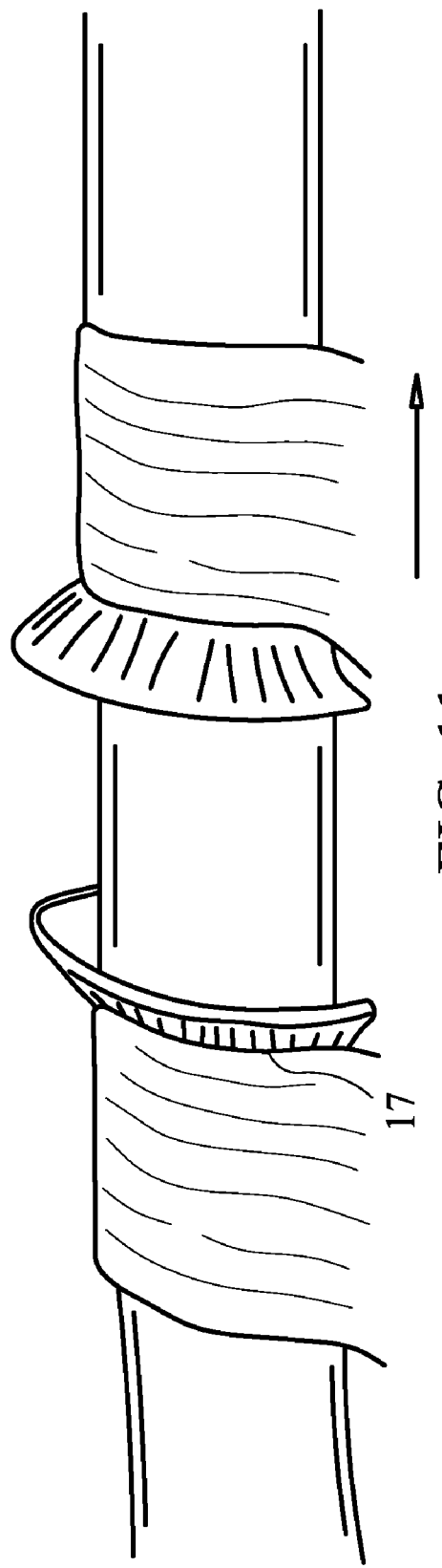

In another example, as illustrated in FIGS. 11c, 11d, and 11e, during finger flexion the repair site 16 must glide partially into a proximally adjacent pulley and partially into a distally adjacent pulley. Under these circumstances, one implantable device 27 is sutured into the proximal pulley, and another implantable device 27 is sutured into the more distal pulley. The implantable devices are positioned so that the respective flared mouths 24 of each device would face each other, thereby facilitating the passage of a bulky repair site 16 through the pulley edges 17 located proximally adjacent and distally adjacent to the repair site.

Figure 12A:
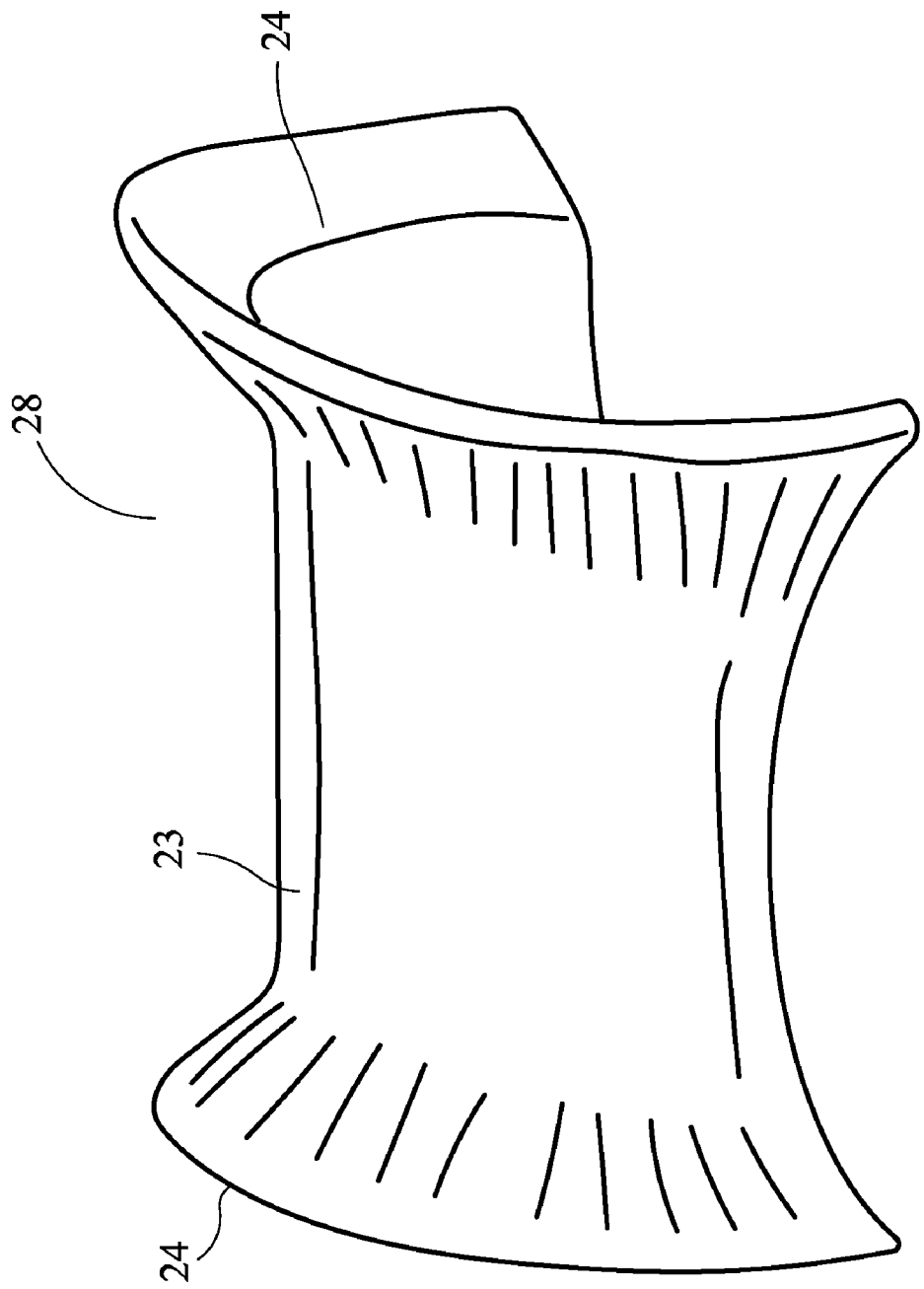
FIG. 12a is a lateral view of a double-ended implantable embodiment of the present invention having two flared mouths.

Another embodiment of the present invention, as illustrated in FIG. 12a, is a double-ended implantable device 28 comprised of a hollow member, preferably shaped as a cylindrical tube or barrel cut in half along its longitudinal axis, having an inner and outer surface, a shaft 23, and two flared mouths 24, one at each end of the shaft 23. As depicted in FIG. 12a, the inner surface is at least in part concave, the outer surface is at least in part convex, and the shaft 23 and each of the flared mouths 24 are at least in part arcuate. With reference to FIG. 12a, the inner surface, the outer surface, the shaft 23, and the flared mouths 24 are at least partially arcuate in planes parallel to the width of the implantable device 28. Furthermore, with reference to FIGS. 12a and 12b, the inner surface, the outer surface, the shaft 23, and the flared mouths 24 are at least partially arcuate in cross section in planes transverse to the direction of passage of the tendon end or repair site.

Figure 12B:
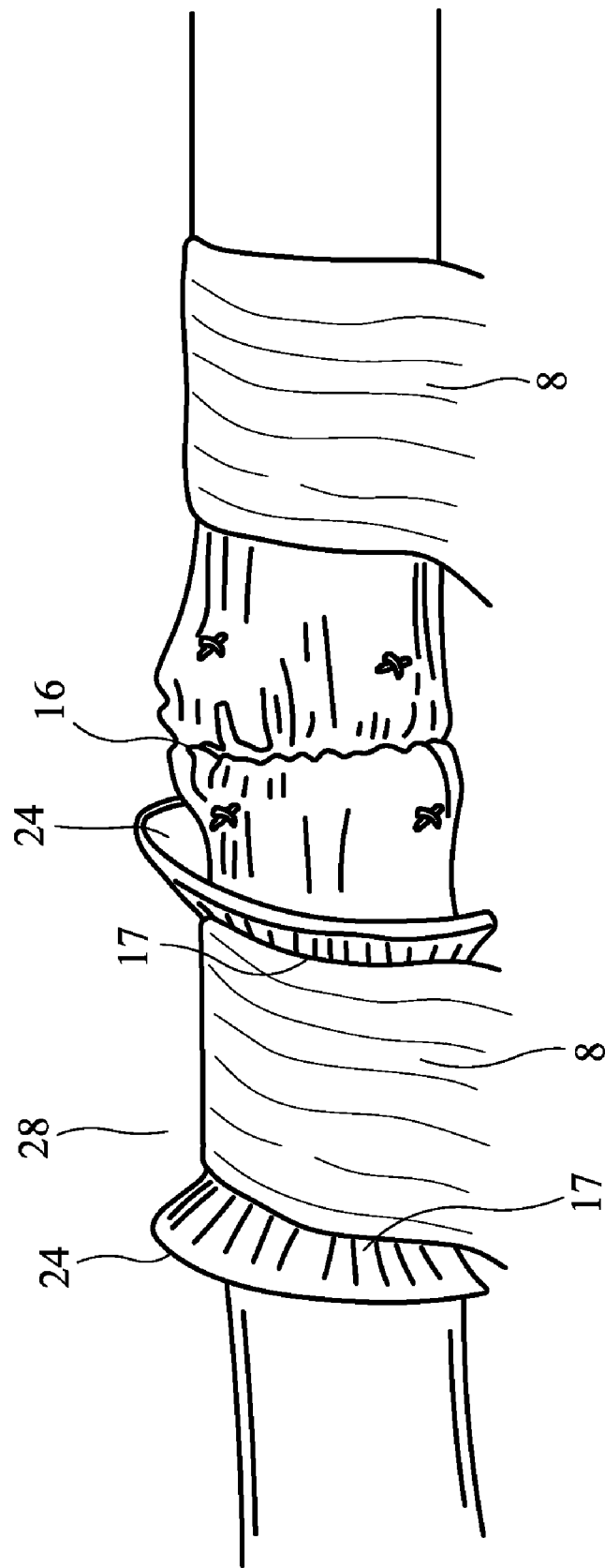
FIG. 12b is a view of a bulky repair site adjacent to a pulley with a double-ended implantable device with two flare mouths traversing the entire length of the pulley.

As illustrated in FIG. 12b, this double-ended implantable device 28 is positioned and sutured into the flexor tendon sheath 8 so that the shaft 23 of the device traverses the entire length of a single pulley, and the device's two flared mouths 24 are positioned at both the distal and proximal edges of the pulley 17, thus facilitating the exit and entrance of the repair site 16 through the device's flared mouths, at both the proximal and distal pulley edges 17 during finger flexion. The double-ended implantable funnel device 28 can be made of a safe, biodegradable material which is known, accepted, and currently used in surgical procedures. Alternatively, the double-ended implantable device 28 can be made of a non-biodegradable material, and can be removed from the patient at a later date when the suture site has sufficiently healed. In another embodiment, the inside of the shaft 23 of the double-ended implantable 28 device can be coated or lubricated with a non-hazardous, slick material that would minimize resistance between the shaft 23 of the device and the repair site 16, thereby improving the tendon's gliding function. In another embodiment, the double-ended implantable device 28 may also include a detachable, elongated handle attached to the shaft 23 which would allow the surgeon to manipulate the device into a desired location.

In yet another embodiment, the double-ended implantable device 28 could also be used to repair and reconstruct an acute or chronic flexor tendon sheath pulley by suturing the double-ended implantable device 28 to the periosteum of the anterolateral and anteromedial ridges of the corresponding phalanx, 10, 11, and/or 12, or alternatively, by affixing the double-ended implantable device 28 to the periosteum of the anterolateral and anteromedial ridges of the corresponding phalanx, 10, 11, and/or 12, with small screws screwed into the bone.

The invention claimed is:

1. A method of passing a tendon end through a flexor tendon sheath comprising:
   providing a surgical device comprising a member having a flared mouth, a length, a width perpendicular to the length, an inner surface, and an outer surface opposite the inner surface, the flared mouth adapted to prevent an edge of a pulley of the flexor tendon sheath from having excessive contact with the tendon end, and the outer surface and the flared mouth each being at least in part arcuate in a plane parallel to the width;
   inserting at least a portion of the member into a position within the pulley to contact the outer surface with an interior portion of the pulley and contacting the flared mouth with the edge of the pulley, the flared mouth defining an entrance to a passage through the pulley;
   inserting the tendon end into the entrance to the passage; and
   passing the tendon end through the passage while maintaining the position of the member with respect to the pulley.

2. The method of claim 1, wherein the member further comprises an apical end opposite the flared mouth.

3. The method of claim 1, wherein the method is repeated for a plurality of pulleys until the tendon end reaches a desired location along the flexor tendon sheath.

4. The method of claim 1, further comprising suturing the surgical device to the pulley.

5. The method of claim 1, further comprising enlarging the space within which the tendon end enters the pulley.

6. The method of claim 1, wherein the surgical device is an implant.

7. The method of claim 1, wherein the inner surface is at least in part concave and the outer surface is at least in part convex.

8. The method of claim 1, wherein the flared mouth is at least in part arcuate.

9. The method of claim 1, wherein the member is at least partially arcuate in cross section in a plane transverse to the direction of passage of the tendon end.

10. A method of passing a repair site through a flexor tendon sheath comprising:
providing a surgical device comprising a member having a length, a width perpendicular to the length, an inner surface, an outer surface opposite the inner surface, and a flared mouth at an end of the member, the outer surface and the flared mouth each being at least in part arcuate in a plane parallel to the width;
positioning at least a portion of the member within a pulley of the flexor tendon sheath to contact the outer surface of the surgical device with the pulley, and positioning the flared mouth directly adjacent an edge of the pulley,
preventing the repair site from having excessive contact with the edge of the pulley using the flared mouth during finger flexion while maintaining the position of the member with respect to the pulley.

11. The method of claim 10, wherein the member of the surgical device further comprises a shaft and an apical end.

12. The method of claim 10, wherein the surgical device is sutured to the pulley.

13. The method of claim 10, wherein the method is repeated for each pulley edge that the repair site must traverse during finger flexion.

14. The method of claim 10, further comprising enlarging the space within which the repair site enters the pulley.

15. The method of claim 10, wherein the surgical device is an implant.

16. The method of claim 10, wherein the inner surface is at least in part concave and the outer surface is at least in part convex.

17. The method of claim 10, wherein the flared mouth is at least in part arcuate.

18. A method of passing a repair site through a flexor tendon sheath comprising:
providing a surgical device comprising a shaft having a first end, a second end, a length between the first and second ends, and a width perpendicular to the length, the shaft being at least in part arcuate in a plane parallel to the width, the shaft having a first flared mouth at the first end, a second flared mouth at the second end, an inner surface, and an outer surface opposite the inner surface, the first and second flared mouths each being at least in part arcuate in a plane parallel to the width of the shaft, the inner and outer surfaces extending between the first and second ends;
inserting at least a portion of the surgical device into a pulley in the flexor tendon sheath; and
positioning the first flared mouth adjacent a first edge of the pulley, positioning the second flared mouth adjacent a second edge of the pulley, the first and second flared mouths preventing the first and second edges, respectively, of the pulley from excessive contact with the repair site, wherein during finger flexion and movement of the repair site relative to the pulley, the repair site enters the first flared mouth, is compressed into the shaft, and exits the second flared mouth.

19. The method of claim 18, wherein the surgical device is sutured to the pulley.

20. The method of claim 18, further comprising enlarging the space within which the repair site enters the pulley.

21. The method of claim 18, wherein the surgical device is an implant.

22. The method of claim 18, wherein the inner surface is at least in part concave and the outer surface is at least in part convex.

23. The method of claim 18, wherein one of the first and second flared mouths is at least in part arcuate.

* * * * *

UNITED STATES PATENT AND TRADEMARK OFFICE
CERTIFICATE OF CORRECTION

PATENT NO. : 8,075,575 B2
APPLICATION NO. : 11/962867
DATED : December 13, 2011
INVENTOR(S) : Gonzalez-Hernandez It is certified that error appears in the above-identified patent and that said Letters Patent is hereby corrected as shown below:

<u>Title Page 1, Item (56), Other Publications, Column 2:</u>
line 10: change "Gonzalez-Hernandez" to -- Gonzalez-Hernandez. --;
line 11: change "Tendonel®" to -- Tendone!® --; and
line 12: change "2 pages. ." to -- 2 pages. --.

<u>Title Page 2, Item (56), Other Publications, Column 2:</u>
line 3: change "Shealth" to -- Sheath --; and
line 9: change "SEarch" to -- Search --.

Signed and Sealed this
Thirty-first Day of July, 2012

David J. Kappos
*Director of the United States Patent and Trademark Office*